(12) United States Patent
Seyler et al.

(10) Patent No.: US 8,581,020 B2
(45) Date of Patent: Nov. 12, 2013

(54) TRANSFER LAYER FOR ABSORBENT ARTICLE

(75) Inventors: Rickey J. Seyler, Chesterfield, VA (US); Gregory M. Rieker, Columbus, IN (US)

(73) Assignee: Tredegar Film Products Corporation, Richmond, VA (US)

(*) Notice: Subject to any disclaimer, the term of this patent is extended or adjusted under 35 U.S.C. 154(b) by 585 days.

(21) Appl. No.: 12/695,326

(22) Filed: Jan. 28, 2010

(65) Prior Publication Data

US 2011/0184370 A1    Jul. 28, 2011

(51) Int. Cl.
*A61F 13/15* (2006.01)
(52) U.S. Cl.
USPC .................................. 604/383; 604/385.101
(58) Field of Classification Search
USPC .................................. 604/378, 383, 385.101
See application file for complete search history.

(56) References Cited

U.S. PATENT DOCUMENTS

| | | | |
|---|---|---|---|
| 3,929,135 A | 12/1975 | Thompson | |
| 3,945,386 A | 3/1976 | Anczurowski | |
| 3,967,623 A | 7/1976 | Butterworth | |
| 4,323,069 A | 4/1982 | Ahr | |
| 4,324,247 A | 4/1982 | Aziz | |
| 4,456,570 A | 6/1984 | Thomas et al. | |
| 4,726,976 A | 2/1988 | Karami | |
| 5,078,710 A * | 1/1992 | Suda et al. | 604/383 |
| 5,171,238 A | 12/1992 | Kajander | |
| 5,342,334 A | 8/1994 | Thompson | |
| 5,352,217 A | 10/1994 | Curro | |
| 5,368,909 A | 11/1994 | Langdon | |
| 5,387,209 A * | 2/1995 | Yamamoto et al. | 604/384 |
| 5,439,458 A | 8/1995 | Noel | |
| 5,509,915 A | 4/1996 | Hanson | |
| 5,533,991 A * | 7/1996 | Kirby et al. | 604/383 |
| 5,603,707 A | 2/1997 | Trombetta | |
| 5,614,283 A | 3/1997 | Potnis | |
| 5,643,240 A | 7/1997 | Jackson | |
| 5,846,230 A | 12/1998 | Osborn, III | |
| 5,897,543 A * | 4/1999 | Francis | 604/383 |
| 6,180,052 B1 | 1/2001 | Ouellette et al. | |
| 6,413,247 B1 * | 7/2002 | Carlucci et al. | 604/385.01 |
| 6,627,791 B1 * | 9/2003 | Veglio et al. | 604/383 |
| 7,858,842 B2 * | 12/2010 | Komatsu et al. | 604/378 |
| 2002/0133132 A1 * | 9/2002 | Copat et al. | 604/383 |
| 2004/0043189 A1 | 3/2004 | Huang | |
| 2010/0121298 A1 * | 5/2010 | Seyler et al. | 604/378 |

FOREIGN PATENT DOCUMENTS

| | | |
|---|---|---|
| EP | 1040801 | 10/2000 |
| EP | 2184041 | 5/2010 |
| WO | WO97/03818 | 2/1997 |
| WO | WO00/16726 | 3/2000 |
| WO | WO2006/041724 | 4/2006 |

OTHER PUBLICATIONS

European Patent Application No. 11150052.6-2124; European Search Report dated May 11, 2011, 6 pages.

* cited by examiner

*Primary Examiner* — Lynne Anderson
(74) *Attorney, Agent, or Firm* — Condo Roccia LLP

(57) ABSTRACT

A film particularly suited for use as a transfer layer in an absorbent article has a plurality of capillaries and a plurality of drains, said capillaries comprising side walls depending from a female side of the film and terminating in an aperture on a male side of the film; said drains comprising side walls that depending from the female side of the film and terminating in an aperture on the male side of the film, wherein the drains are disposed at an obtuse angle relative to a base plane of the film.

35 Claims, 2 Drawing Sheets

TRANSFER LAYER FOR ABSORBENT ARTICLE

BACKGROUND OF THE DISCLOSURE

The disclosure relates to formed films, more specifically three-dimensional formed films for use as transfer layers in absorbent articles.

Absorbent articles are articles that are generally used once or a limited number of times for the temporary collection and immobilization of bodily fluids. Such articles include diapers, adult incontinent products, feminine hygiene products, bandages and similar articles. In general, these articles have a topsheet, which is positioned adjacent the skin of the user, a backsheet, which is opposite the topsheet and may, in use, be positioned adjacent to the clothes of the wearer, and an absorbent core positioned between the topsheet and the backsheet. In most instances, the topsheet is pervious to the bodily fluids and the backsheet is impervious to such fluids, thus protecting the clothing of the wearer from leaks. The absorbent core is designed to collect and hold the bodily fluids until the article can be disposed of and replaced with a fresh article.

Transfer layers, which are also known in the art as acquisition distribution layers or "ADL", have been used in absorbent articles. Both nonwoven webs and three-dimensional formed films have found use as transfer layers in the past. A transfer layer is typically positioned between the topsheet and the absorbent core and generally improves the efficiency of the article to absorb and retain fluids. For example, transfer layers have been used to provide void volume, which serves as a temporary reservoir to collect and hold fluids until the fluids can be absorbed by the core. In addition, transfer layers have been employed to promote lateral flow of fluids in a direction generally parallel to the plane of the transfer layer, thereby permitting more of the core to be used to absorb fluids. See, for example, U.S. Pat. No. 4,324,247.

There is a continuing need for transfer layers that more effectively promote distribution of fluids over the absorbent core, provide more comfort for the wearer, reduce surface wetness in the topsheet, and prevent or reduce rewet.

SUMMARY OF THE DISCLOSURE

In one embodiment, the disclosure provides a formed film for use as a transfer layer, the film having a plurality of three-dimensional capillaries and plurality of three-dimensional drains, wherein the drains are disposed at an obtuse angle relative to the base plane of the film.

In another embodiment, the disclosure provides a formed film for use as a transfer layer, the film having a plurality of three-dimensional capillaries and plurality of three-dimensional drains, wherein the drains are disposed at an obtuse angle relative to the base plane of the film and the capillaries are disposed at an angle approximately normal to the base plane of the film.

In another embodiment, the disclosure provides a formed film for use as a transfer layer, the film having a plurality of three-dimensional capillaries and plurality of three-dimensional drains, wherein the drains are disposed at an obtuse angle relative to the base plane of the film and wherein the drains and the capillaries terminate in a common plane.

These and other embodiments will be apparent from a reading of the detailed description, with reference to the drawings, and the appended claims.

DETAILED DESCRIPTION OF THE EMBODIMENTS

Figure 1:
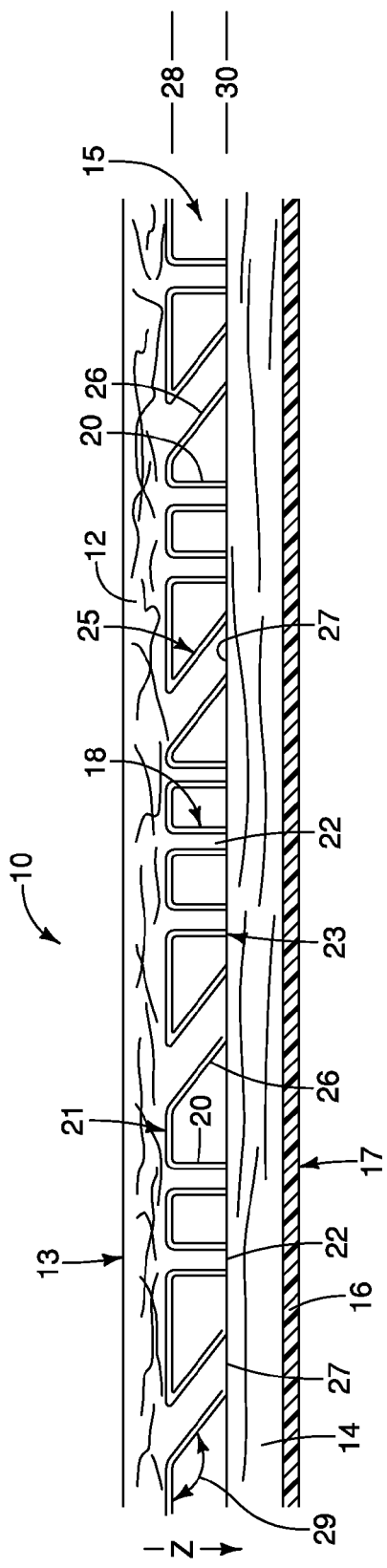
FIG. 1 is a cross-sectional view of an absorbent article having a transfer layer in accordance with an embodiment of the disclosure.

Absorbent articles generally comprise a topsheet, an absorbent core, and a backsheet. The topsheet is on the body facing side of the absorbent article and typically comprises a liquid pervious material that allows liquid from an insult to transfer from the body-facing surface of the absorbent article to the absorbent core. The term "insult" generally refers to an amount of a liquid or the act of adding a liquid on a topsheet of an absorbent article. An insult may occur during product use and during finished product testing. Consequently, "multiple insults" occur when the same absorbent article is insulted more than once. The topsheet is typically in close proximity or even direct contact with the wearer's skin during use and is typically made of a soft material such as a nonwoven material, an apertured film, or a combination of these materials made into a unitary composite. The topsheet is typically designed to retain a comfortable, dry feel to the wearer even after an insult.

The backsheet is positioned on the garment facing side or outside surface of the absorbent article. A backsheet may be a liquid impervious film that does not allow liquid to transfer from within the absorbent article to the exterior surface of the absorbent article or to the garment of the wearer. A breathable backsheet is impervious to liquid, yet allows water vapor to pass out of the absorbent article. This lowers the humidity felt by the wearer and thereby increases the comfort to the wearer.

The absorbent core absorbs the insult and retains the liquid while the absorbent article is in use. The absorbent core should adequately absorb an insult or multiple insults and substantially retain the insult until the absorbent article is removed and discarded. The storage capacity of the absorbent core and the efficiency of distribution of an insult across the absorbent core determine the amount of liquid that may be held in the absorbent article. The absorbent material in an absorbent core may comprise any liquid absorbent material such as, but not limited to, cellulose materials including fibers, cellular sponge or foam materials, super absorbent materials, such as superabsorbent polymers, hydrocolloidal materials, gel materials and combinations thereof. It is within the contemplated scope of the present disclosure that one or more of these types of absorbent materials are useful in embodiments. In particular, in certain embodiments, the absorbent material may comprise a mixture of absorbent granular materials and finely chopped cellulose fibers.

Particularly useful absorbent materials are high absorbency gel-type materials which are generally capable of absorbing about 10 to about 50 times their weight in fluid. As is generally known in the art, the rate at which the core absorbs liquids is inversely proportional to the ability of the core to hold the liquids absorbed. Thus, the superabsorbent materials used in cores are very good at holding liquids, but are relatively slow at liquid uptake. The delay in liquid uptake results in more unabsorbed or free fluid in the article, and thus decreases the rewet performance of the article. Because use of these materials has other benefits, such as reduced bulk of the core, the slower uptake is generally outweighed by the other advantages.

In accordance with the embodiments, the transfer layers are located between the topsheet and the absorbent core or between the backsheet and the absorbent core. Most preferably, the transfer layers are located between the topsheet and the core.

Transfer layers may function to control rewet, a phenomenon whereby unabsorbed or "free" fluid within the article is present on or within the user-contacting surface of the article. Rewet is comprised of a surface wetness component and a back wetting component. Surface wetness refers to liquids that remain on the surface of the topsheet or within the porosity of the topsheet after an insult. Back wetting refers to fluids that have once passed through the topsheet but transfer back to the topsheet surface. Back wetting is generally more pronounced when the article is under load or compression, whereby fluids are forced back through the topsheet. The compression can occur, for example, when an infant urinates in the diaper and then sits. Liquids present at or within the surface of the topsheet, by whatever mechanism, create an unpleasant, damp feeling to the user of the article. Thus, minimizing or eliminating rewet is important for consumer acceptance. Transfer layers can control rewet by providing a physical restriction to back wetting. In particular, a film material acts as a physical barrier because the film itself is liquid impermeable and the apertures are generally shaped to restrict the flow of liquids away from the absorbent core. Nonwoven transfer layers, however, provide a temporary reservoir and collect fluids before they reach the topsheet surface. In certain situations, transfer layers can also reduce surface wetness on the topsheet by facilitating transfer of stationary fluids that would otherwise tend to remain on the topsheet.

In standard industry tests, such as EDANA ERT 151.2-99 or EDANA ERT 151.3-02, rewet is measured by subjecting the article to a measured insult of fluid, waiting 10 minutes, and then applying blotter paper and a weight to the topsheet and measuring the amount of liquid acquired by the blotter paper. The reason for the 10 minute delay is to allow the absorbent core time to acquire the liquid. As a practical matter, however, the user of the article does not want the wet sensation to last for 10 minutes as it can be a very unpleasant feeling. Thus, from a consumer perspective, near instantaneous dryness following an insult is required.

An insult may be considered to include a combination of both dynamic and stationary fluid. The dynamic fluid flows through the topsheet and transfer layer at the time of insult while the stationary fluid may be retained within a porosity of the topsheet and/or transfer layer. To remove the stationary fluid, a transfer layer must be capable of sustaining z-direction wicking or capillary action. When the transfer layer is a three-dimensional formed film, z-direction wicking or capillary action is accomplished by providing at least a portion of the apertures that are sufficiently small in diameter to achieve capillarity or capillary action.

As mentioned, both films and nonwoven fibrous webs have been used as both topsheets and transfer layers. Nonwoven webs have internal void space between the fibers that can attract and hold liquids. Thus, nonwoven webs provide a temporary or "buffer" reservoir for fluids. When an insult occurs, fluids accumulate in the pore spaces of a nonwoven, whether it is used as a topsheet or a transfer layer, until the fluids have an opportunity to drain out and/or be absorbed by the core. The buffer function of the nonwoven works in both directions. Specifically, when an insult occurs, the nonwoven acts as a buffer to hold fluids until they can drain out and be absorbed by the core. Once the fluids have drained out, the nonwoven can act as a buffer to accumulate fluids before they reach the topsheet surface. The amount of fluids that drain out, and the time to do so, as well as the buffer capacity of the nonwoven are dependent upon the size of the pores between the fibers of the nonwoven web, the relative hydrophilicity/hydrophobicity of the nonwoven, the fiber density, and other factors. Immediately after an insult, the void capacity of the nonwoven is essentially full and the core has not had sufficient time to absorb the insult. Thus, there is no capacity for the nonwoven to act as a buffer to fluids transferring back to the topsheet surface. The portion of the insult that passes through the nonwoven web but is not yet absorbed, as well as the portion that is temporarily retained within the pores of the web can contribute to rewet.

With a formed film, however, except for a small amount of fluid that might remain in the land areas between the apertures, the insult is nearly instantaneously passed through the film and stored in the void space on the underside of the film. If a load is applied at that time, the film acts as a physical barrier to rewet and it is only the fluids that find their way back through the apertures that contribute to rewet. Because the apertures in formed films are typically tapered to have a narrower opening on one side (i.e.; the "male" side) verses the opposite or "female" side, the films exhibit a preferential liquid flow towards the core and are practically liquid impervious in the opposite direction. As a result, formed films can provide near instantaneous dryness in an absorbent article whereas nonwoven webs do not. Indeed, testing has shown that films are superior to nonwoven webs in rewet performance, particularly when tested immediately after an insult. With the passage of time following an insult, the nonwoven has an opportunity to drain out and can again function as a buffer to fluid transfer from the core area to the topsheet surface. Thus, the difference in rewet performance when using films as opposed to nonwoven webs is less significant as time after insult increases.

Reported in Table 1 are the grams of liquid obtained using a standard rewet test procedure as a function of time after insult.

TABLE 1

| sample | Time (minutes after insult) | | | | | |
| --- | --- | --- | --- | --- | --- | --- |
| | 0 | 2 | 4 | 6 | 8 | 10 |
| Size 4 diaper with nonwoven transfer layer (first insult) | 16.32 | 0.51 | 0.50 | 0.30 | 0.24 | 0.32 |
| Size 4 diaper with film transfer layer (first insult) | 1.37 | 0.29 | 0.34 | 0.32 | 0.22 | 0.21 |
| Size 4 diaper with nonwoven transfer layer (third insult) | 48.65 | 32.71 | 22.31 | 17.68 | 20.05 | 12.97 |
| Size 4 diaper with film transfer layer (third insult) | 24.59 | 14.25 | 9.17 | 5.43 | 5.34 | 4.77 |

Figure 2:
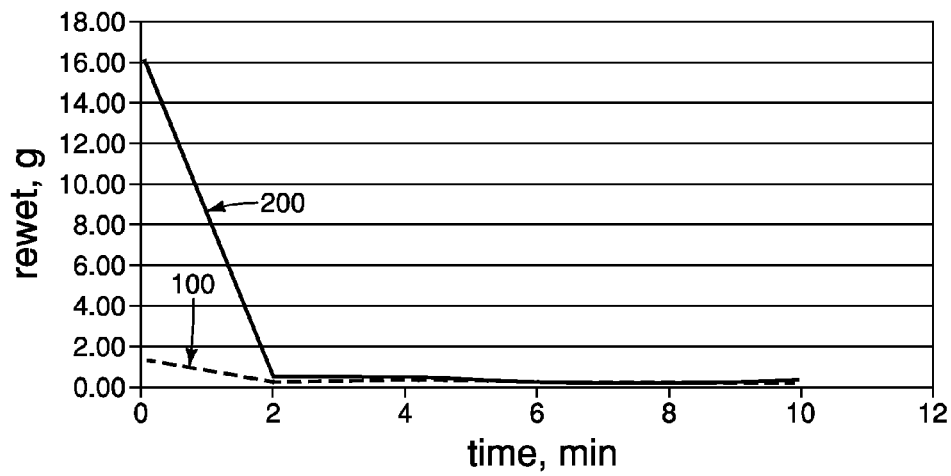
FIG. 2 is a graph of grams of liquid versus time.
Figure 3:
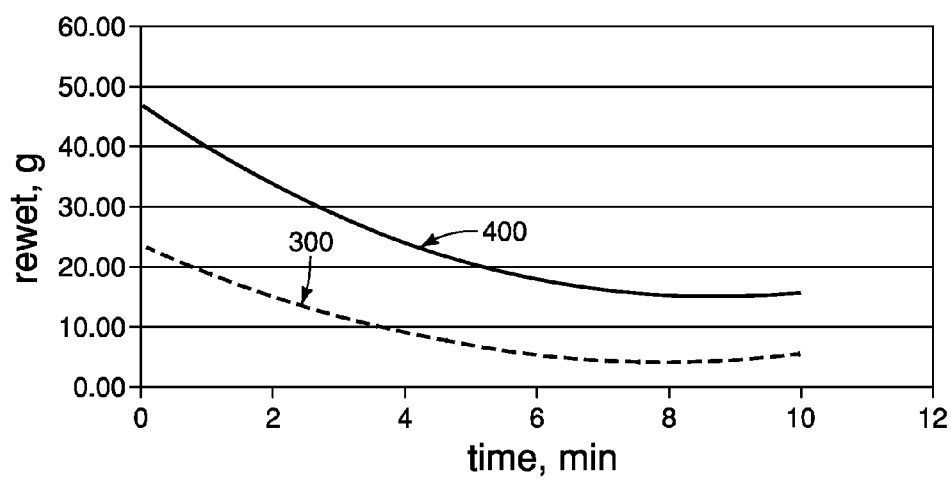
FIG. 3 is a graph of grams of liquid versus time

The data from Table 1 is plotted and illustrated in FIGS. 2 and 3 as graphs of grams of fluid versus time. More specifically, FIG. 2 depicts results obtained when measuring rewet after acquisition of a first insult. Curve 100 represents an article using a film and curve 200 represents an article using a nonwoven. As seen in FIG. 2, the use of a film results in significantly less rewet immediately after insult as compared to using a nonwoven. In time, the difference between films and nonwovens is negligible, but films clearly provide a more immediate sensation of dryness. These data indicate that immediately after a first insult, baby diapers using nonwoven transfer layers can produce 6-16 grams more liquid in the rewet test as compared to identical articles using formed films.

With reference to FIG. 3, illustrated therein is a curve of grams liquid versus time of a rewet test after a third insult. The data show that articles using formed films as transfer layers (curve 300) showed significantly less surface liquids as compared to articles using nonwovens as transfer layers (curve 400). The difference is similar to that seen in the conditions for FIG. 2; i.e., the articles using formed films had 6-26 grams less liquid versus articles using nonwoven webs.

Transfer layers in accordance with the embodiments are films. As used herein, a "film" refers to a thin polymer sheet or web. A film may be produced, for example, by extruding a molten thermoplastic polymer in a cast or blown extrusion process and may be further processed between rollers and cooled to form the web. Films can be monolayer films or coextruded films, for example.

The term "polymer" includes homopolymers, copolymers, such as, for example, block, graft, random and alternating copolymers, terpolymers, etc., and blends and modifications thereof. Furthermore, unless otherwise specifically limited, the term "polymer" is meant to include all possible geometrical configurations of the material, such as isotactic, syndiotactic and atactic or random symmetries.

The transfer layers may be dimensionally described as having a machine direction, a cross direction, and a z-direction. The machine direction is defined by the direction in which the film passes through the manufacturing process. Typically, films are produced as long sheets or webs having a much greater length than width. In such a case, the machine direction is usually the length (also referred to as the x-direction) of the sheet. Perpendicular to the machine direction is the cross direction or transverse direction (also referred to as the y-direction or width) of the sheet. The thickness of the film (sometimes also referred in certain embodiments as loft or caliper of the film) is measured in the z-direction.

Three-dimensional formed films include a base plane forming the nominal thickness of the film, and include structures originating on the surface of the film and protruding outwardly in the z-direction. The dimensions of these structures provide the film with a z-direction dimension that is greater than the nominal thickness of the film. They also provide the film with a secondary plane defined by the surface structures and spaced from the base plane of the film in the z-direction. The three-dimensional features of the three-dimensional formed films may be produced in an embossing process, a hydroforming process, or a vacuum forming process, for example. All such processes are well known in the art.

A "multiplanar film" is a three-dimensional formed film that has additional surface structures that originate from both the base plane and the secondary plane of the film. For example, a formed film having a multiplanar structure may comprise a plurality of plateaus that are on the surface of the film, the plateaus defining at least one additional plane of the film above or below the base surface. In certain embodiments of the multiplanar three-dimensional formed film, protuberances may be formed on any or all of the available planes.

A three-dimensional apertured formed film is simply a formed film that has openings or apertures in the three-dimensional structures. The size, spacing and other properties of the apertured three-dimensional structures are based upon the particular apparatus used to create the three-dimensional apertured formed film. For example, in a vacuum forming process, a hydroforming process, and some mechanical processes, the size, shape and spacing of the apertures is determined by the forming structure that supports the film while the film is subjected to vacuum pressure, pressurized water streams, or mechanical perforation devices such as pins. See, for example U.S. Pat. No. 4,456,570 and U.S. Pat. No. 3,929,135.

For apertured formed films, the z-direction dimension of the three-dimensional structure is a function of the diameter of the three-dimensional structure, which, in turn, is a function of the diameter of the apertures in the forming structure or the diameter of the perforating pin. For example, smaller diameter structures typically have a smaller z-direction dimension as compared to larger diameter structures. Other factors also contribute to the z-direction height of the three-dimensional features such as film composition, basis weight of the film, temperature of the film while being apertured, as well as other process conditions and apparatus-related factors.

For example, three-dimensional formed films may comprise at least one polymer selected from polyolefins (e.g., $C_2$-$C_{10}$ olefins such as polyethylene, polypropylene, etc.); polyesters; plastomers; polyamides (e.g., nylon); polystyrenes; polyurethanes; vinyl polymers; acrylic and/or methacrylic polymers; elastomers (e.g., styrene block copolymer elastomers); polymers from natural renewable sources; biodegradable polymers; and mixtures or blends thereof. Preferably, the polymer is a thermoplastic polymer.

Additionally, any of a variety of additives may be added to the polymers and may provide certain desired characteristics, including, but not limited to, roughness, reduction of anti-static charge build-up, abrasion resistance, printability, writeability, opacity, hydrophilicity, hydrophobicity, processibility, UV stabilization, color, etc. Such additives are well known in the industry and include, for example, calcium carbonate (abrasion resistance), titanium dioxide (color and opacity) and silicon dioxide (roughness), surfactants (hydrophilicity/hydrophobicity), process aids (processibility), etc.

Referring to the embodiment of FIG. 1, absorbent article 10 comprises a topsheet 12, a core 14, a backsheet 16 and a transfer layer 15 positioned between the core 14 and topsheet 12. The article 10 has a body facing surface 13 which, in use, would be placed adjacent to or otherwise in close proximity with the skin of the user. The article 10 also has a garment facing surface 17 which is opposite the body facing surface 13. The garment facing surface 17, in use, would be in proximity to the garment of the user or to the environment if the absorbent article is a bandage, wound dressing, surgical drape or the like.

Topsheet 12 comprises a fluid pervious material to allow fluids to enter the absorbent article 10. Topsheet 12 is generally an apertured film, such as an apertured formed film, a nonwoven web, or composites. In the embodiments illustrated, the topsheet 12 comprises a nonwoven web. Backsheet 16 is generally fluid impervious to prevent leakage of fluids from the absorbent article. Films, nonwoven webs and composites are typically used for the backsheet. In the embodiments shown, the backsheet 16 comprises a liquid impervious blown or cast film. The absorbent core 14 is between the topsheet 12 and the backsheet 16 and comprises materials that can absorb and retain fluids that pass through the topsheet until the article is discarded.

As seen in FIG. 1, the transfer layer 15 comprises a three-dimensional formed film having a plurality of three-dimensional capillaries 18 and plurality of three-dimensional drains 25. The capillaries 18 comprise protuberances comprising cone-shaped structures with side walls 20 that originate on the female side 21 of the film 15 and extend in a z-direction (indicated by arrow "Z" in FIG. 1) from the female side 21 of the film 15. The capillaries 18 terminate in an aperture 22 on the male side 23 of the film 15.

Capillaries 18 are sized to provide fluid transport via capillary action and promote removal of a stationary portion of the insult retained on the topsheet surface or within the porosity of the topsheet by providing sustained z-direction wicking. The z-direction wicking improves rewet performance by reducing either the surface wetness component or the back wetting component, or both. This z-direction wicking is accomplished by providing the capillaries 18 with a diameter that is sufficiently small to achieve capillarity.

For sustained capillary action to occur, it is necessary to provide some mechanism to remove fluids from the exit side (i.e., at aperture 22) of the capillary 18. One convenient mechanism in absorbent articles is to place the exit side of the capillary in intimate contact with the absorbent core. This has been difficult to execute in prior art transfer layers, however, particularly in those transfer layers also containing larger diameter protuberances. Specifically, the larger diameter protuberances, which are necessary to provide for rapid acquisition of the dynamic portion of an insult, would generally be of greater dimension in the z-direction than the smaller diameter capillaries. Accordingly, for the capillaries to make intimate contact with the core, the larger protuberances would need to be crushed for achieving intimate contact. This is, of course, contraindicated because it defeats the purpose of the larger protuberances. Accordingly, in prior art films, the capillaries would be suspended above the absorbent core in the void (i.e., empty) space and thus fail to provide for sustainable removal of liquid.

The transfer layer 15 further includes a plurality of drains 25. The drains 25 are three-dimensional structures having side walls 26 that originate on the female side 21 of the film 15 and extend in the z-direction as seen in FIG. 1. The drains 25 terminate in an aperture 27 on the male side 22 of the film 15. The drains 25 are of a larger diameter than the capillaries 18 and permit the rapid transfer of fluids from the female side 21 of the film 15 to the male side 23 of the film.

As seen in FIG. 1, the drains 25 are oriented to form an angle 29 relative to the base plane 28 of the film 15. The angle 29 is greater than 90 degrees relative to the base plane 28, such that drains 25 form an obtuse angle relative to the base plane 28 of the film 15. The angle 29 is not particularly important, and may generally be in the range of 100-175° relative to the base plane 28. Films having such angular protrusions are known in the art and disclosed, for example, in EP 1040801; WO 1997/003818; and WO 2000/016726, each of which is incorporated herein by reference.

Because drains 25 are disposed at an obtuse angle relative to the base plane 28 of the film 15, the drains do not extend in the z-direction as much as they would if they were oriented normal to the base plane 28. Accordingly, the angular orientation of the drains 25 permits the apertures 22 of the capillaries 18 to remain in intimate contact with the core 14, which provides the mechanism needed to maintain sustained capillary action in wicking fluids away from topsheet 12. Stated differently, as seen in FIG. 1, the drains 25 and capillaries 18 all terminate in a common plane 30 that is generally parallel to and spaced from the base plane 28 of the film 15.

The angled orientation of the drains 25 also serves to at least partially occlude the sight line through the film 15 to the core layer 14. Accordingly, the films 15 also serve a masking function in at least partially hiding the core 14.

The drains 25 may be any desired size that permits rapid passage of the fluids. For example, the drains 25 of certain embodiments may have an average cross sectional area greater than 0.2 mm² and an average hydraulic diameter between 0.55 mm and 1.2 mm. The capillaries 18, by contrast, have an average diameter between 50 microns and 400 microns as measured on the female side 21. The ratio of the hydraulic radius of the drains 25 to the capillaries 18 will generally exceed 3:1 and in most cases will be 4 or 5:1 or higher. Ratios of 10:1 or more are also common.

In the embodiment shown in FIG. 1, the capillaries 18 and drains 25 are generally conical. However, is it to be understood that the shape of these structures is not particularly significant. In particular, the capillaries and drains may have a shape that is circular, oval, triangular, square, pentagonal, hexagonal, or any other desired shape.

The transfer layer may be oriented in the absorbent article with either the male side or female side facing the absorbent core. In many applications, the male side of the transfer layer will face the absorbent core, but in some applications it may be desirable for the female side to face the core.

Any design or pattern may be formed to produce embodiments of the transfer layer. Any ratio of drains to capillary-sized protuberances may be used. Depending on the applications, more or fewer capillary-sized structures may be desired as compared to the embodiments illustrated in FIG. 1.

It is to be understood that although this disclosure describes several embodiments, various modifications apparent to those skilled in the art may be made without departing from the invention as described in the specification and claims herein.

The invention claimed is:

1. A formed film having a female side and a male side, the formed film comprising:
    a plurality of capillaries extending from the female side of the formed film and terminating in one or more apertures on the male side of the formed film; and
    a plurality of drains extending from the female side of the formed film and terminating in one or more apertures on the male side of the formed film, wherein the plurality of drains are disposed at an obtuse angle relative to a base plane of the formed film and slant in an angular orientation that is the same for each drain, wherein the plurality of drains slanted in the angular orientation extend from the female side toward the male side in a z-direction about the same as the plurality of capillaries such that the plurality of drains and the plurality of capillaries terminate in a common plane that is generally parallel and spaced from the base plane, and wherein the angular orientation of the slant of the plurality of drains is different than an orientation of the plurality of capillaries.

2. The formed film of claim 1, wherein the plurality of drains are oriented at an angle of 100-175° relative to the base plane of the formed film.

3. The formed film of claim 1, wherein the plurality of drains have an average cross sectional area greater than 0.2 mm² and an average hydraulic diameter between 0.55 mm and 1.2 mm.

4. The formed film of claim 1, wherein the plurality of capillaries have an average diameter between 50 microns and 400 microns as measured on the female side of the film.

5. The formed film of claim 1, wherein the ratio of the hydraulic radius of the plurality of drains to the plurality of capillaries is greater than 3:1.

6. The formed film of claim 1, wherein the plurality of drains and the plurality of capillaries comprise side walls, and wherein at least one side wall of a drain is parallel to at least another side wall of another drain and not parallel to the side walls of the plurality of capillaries.

7. The formed film of claim 1, wherein the diameter of the plurality of drains is larger than the diameter of the plurality of capillaries.

8. The formed film of claim 1, wherein plurality of drains and the plurality of capillaries are generally conical.

9. An absorbent article comprising:
    a topsheet;
    a core; and a transfer layer comprising a formed film having a plurality of capillaries and a plurality of drains, the plurality of capillaries extending from a female side of the formed film and terminating in one or more apertures that are in intimate contact with the core on a male side of the formed film and the plurality of drains extending from the female side of the formed film and terminating in one or more apertures on the male side of the film, wherein the plurality of drains are disposed at an obtuse angle relative to a base plane of the formed film and slant in an angular orientation that is the same for each drain, wherein the plurality of drains slanted in the angular orientation extend from the female side toward the male side in a z-direction about the same as the plurality of capillaries such that the plurality of drains and the plurality of capillaries terminate in a common plane that is generally parallel and spaced from the base plane, and wherein the angular orientation of the slant of the plurality of drains is different than an orientation of the plurality of capillaries.

10. The absorbent article of claim 9, wherein the plurality of drains are oriented at an angle of 100-175° relative to the base plane of the formed film.

11. The absorbent article of claim 9, wherein the plurality of drains have an average cross sectional area greater than 0.2 mm$^2$ and an average hydraulic diameter between 0.55 mm and 1.2 mm.

12. The absorbent article of claim 9, wherein the plurality of capillaries have an average diameter between 50 microns and 400 microns as measured on the female side of the formed film.

13. The absorbent article of claim 9, wherein the ratio of the hydraulic radius of the plurality of drains to the capillaries is greater than 3:1.

14. The absorbent article of claim 9, wherein the transfer layer is positioned between the topsheet and the core.

15. The absorbent article of claim 14, wherein the female side of the transfer layer is closer to the topsheet than the male side.

16. The absorbent article of claim 9, further comprising a backsheet positioned between the core and the backsheet.

17. The absorbent article of claim 9, wherein the plurality of drains and the plurality of capillaries comprise side walls, and wherein at least one side wall of a drain is parallel to at least another side wall of another drain and not parallel to the side walls of the plurality of capillaries.

18. An absorbent article comprising:
a topsheet;
a transfer layer adjacent to the topsheet, the transfer layer comprising a vacuumed formed film having a female side and a male side, the vacuumed formed film comprising a plurality of capillaries extending in a z-direction from the female side and terminating in apertures on the male side and a plurality of drains extending in the z-direction from the female side and terminating in apertures on the male side, wherein the plurality of drains are disposed at an obtuse angle relative to a base plane of the vacuumed formed film and slant in an angular orientation, wherein the slant in the angular orientation is the same for each of the plurality of drains and different than the plurality of capillaries, and wherein the plurality of drains slanted in the angular orientation extend in the z-direction about the same as the plurality of capillaries such that the plurality of drains and the plurality of capillaries terminate in a common plane that is generally parallel and spaced from the base plane;
an absorbent core adjacent to the transfer layer opposite of the topsheet, wherein the apertures of the plurality of capillaries are in intimate contact with the absorbent core; and
a backsheet adjacent to the absorbent core opposite of the transfer layer such that the absorbent core is positioned between the transfer layer and the backsheet.

19. A formed film having a female side and a male side, the formed film comprising:
a plurality of capillaries extending from the female side of the formed film and terminating in one or more apertures on the male side of the formed film, the plurality of capillaries comprising sidewalls; and
a plurality of drains comprising sidewall and extending from the female side of the formed film and terminating in one or more apertures on the male side of the formed film, the plurality of drains comprising sidewalls, wherein at least one side wall of a drain is parallel to at least another side wall of another drain and not parallel to the side walls of the plurality of capillaries, wherein the plurality of drains are disposed at an obtuse angle relative to a base plane of the formed film and slant in an angular orientation that is the same for each drain, and wherein the plurality of drains slanted in the angular orientation extend from the female side toward the male side in a z-direction about the same as the plurality of capillaries such that the plurality of drains and the plurality of capillaries terminate in a common plane that is generally parallel and spaced from the base plane.

20. The formed film of claim 19, wherein the plurality of drains are oriented at an angle of 100-175° relative to the base plane of the formed film.

21. The formed film of claim 19, wherein the plurality of drains have an average cross sectional area greater than 0.2 mm$^2$ and an average hydraulic diameter between 0.55 mm and 1.2 mm.

22. The formed film of claim 19, wherein the plurality of capillaries have an average diameter between 50 microns and 400 microns as measured on the female side of the film.

23. The formed film of claim 19, wherein the ratio of the hydraulic radius of the plurality of drains to the plurality of capillaries is greater than 3:1.

24. The formed film of claim 19, wherein the angular orientation of the slant of the plurality of drains is different than an orientation of the plurality of capillaries.

25. The formed film of claim 19, wherein the diameter of the plurality of drains is larger than the diameter of the plurality of capillaries.

26. The formed film of claim 19, wherein plurality of drains and the plurality of capillaries are generally conical.

27. An absorbent article comprising:
a topsheet;
a core; and
a transfer layer comprising a formed film having a plurality of capillaries and a plurality of drains, the plurality of capillaries extending from a female side of the formed film and terminating in one or more apertures that are in intimate contact with the core on a male side of the formed film and the plurality of drains extending from the female side of the formed film and terminating in one or more apertures on the male side of the film, and the plurality of drains and the plurality of capillaries comprising side walls, wherein at least one side wall of a drain is parallel to at least another side wall of another drain and not parallel to the side walls of the plurality of capillaries, wherein the plurality of drains are disposed at an obtuse angle relative to a base plane of the formed film and slant in an angular orientation that is the same for each drain, and wherein the plurality of drains slanted in the angular orientation extend from the female side toward the male side in a z-direction about the same as the plurality of capillaries such that the plurality of drains and the plurality of capillaries terminate in a common plane that is generally parallel and spaced from the base plane.

28. The absorbent article of claim 27, wherein the plurality of drains are oriented at an angle of 100-175° relative to the base plane of the formed film.

29. The absorbent article of claim 27, wherein the plurality of drains have an average cross sectional area greater than 0.2 mm$^2$ and an average hydraulic diameter between 0.55 mm and 1.2 mm.

30. The absorbent article of claim 27, wherein the plurality of capillaries have an average diameter between 50 microns and 400 microns as measured on the female side of the formed film.

31. The absorbent article of claim 27, wherein the ratio of the hydraulic radius of the plurality of drains to the capillaries is greater than 3:1.

32. The absorbent article of claim 27, wherein the transfer layer is positioned between the topsheet and the core.

33. The absorbent article of claim 32, wherein the female side of the transfer layer is closer to the topsheet than the male side.

34. The absorbent article of claim 27, further comprising a backsheet positioned between the core and the backsheet.

35. The absorbent article of claim 27, wherein the angular orientation of the slant of the plurality of drains is different than an orientation of the plurality of capillaries.

\* \* \* \* \*